(12) United States Patent
O'Lenick et al.

(10) Patent No.: US 8,273,920 B1
(45) Date of Patent: Sep. 25, 2012

(54) ACETYLENIC QUATERNARY SURFACTANTS

(75) Inventors: Kevin O'Lenick, Dacula, GA (US); Anthony J. O'Lenick, Jr., Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 201 days.

(21) Appl. No.: 12/807,316

(22) Filed: Sep. 3, 2010

Related U.S. Application Data

(60) Provisional application No. 61/337,253, filed on Feb. 2, 2010.

(51) Int. Cl.
*C07C 211/62* (2006.01)

(52) U.S. Cl. .......................... 564/294; 564/224; 564/292
(58) Field of Classification Search ................... 564/224, 564/292, 294
See application file for complete search history.

(56) References Cited

U.S. PATENT DOCUMENTS 5,650,543 A 7/1997 Medina

*Primary Examiner* — Brian J Davis

(57) ABSTRACT

The surfactants of this invention are quaternary ammonium compounds based upon 2,4,7,9-tetramethyl-5-decyne-4,7-diol. These surfactants, not only decrease the surface tension of aqueous systems, but by virtue of the cationic nitrogen containing moiety have outstanding substantivity for hair, skin and textile fibers, lacking in the parent non-ionic.

8 Claims, No Drawings

ACETYLENIC QUATERNARY SURFACTANTS

RELATED APPLICATIONS

This application claims priority to and benefit of U.S. Provisional Application No. 61/337,253 filed Feb. 2, 2010, the disclosure of which is incorporated herein for all purposes.

The surfactants of this invention are quaternary ammonium compounds based upon 2,4,7,9-tetramethyl-5-decyne-4,7-diol. These surfactants, not only decrease the surface tension of aqueous systems, but by virtue of the cationic nitrogen containing moiety have outstanding substantivity for hair, skin and textile fibers, lacking in the parent non-ionic.

BACKGROUND OF THE INVENTION

Ether amines are known materials conforming to the following structure:

$$R-O-(CH_2)_3-NH_2$$

The R group is alkyl, most commonly decyl. These materials are offered by Tomah Products. These materials have not enjoyed acceptance in the personal care market.

A compound of much promise in the development of low surface tension surfactants is 2,4,7,9-tetramethyl-5-decyne-4,7-diol. It has an acetylenic bound in the center, which conforms upon it the properties of lowering surface tension. This material conforms to the following structure;

$$(CH_3)_2-CH-CH_2-\underset{\underset{OH}{|}}{C(CH_3)}-C\equiv C-\underset{\underset{OH}{|}}{C(CH_3)}-CH_2-CH-(CH_3)_2$$

This material has a CAS number of 126-86-3.

Cationic versions of these materials are heretofore unknown.

U.S. Pat. No. 5,650,543 issued Jul. 22, 1997 to Medina entitled Ethoxylated acetylenic glycols having low dynamic surface tension discloses ethoxylated acetylenic glycol compositions having from 4-12 moles of alkylene oxide present. These ethoxylated acetylenic diols, which are raw materials used in the preparation of the compounds of the present invention are said to be excellent as surfactants alone or admixed with other surfactants for use in water borne coatings. U.S. Pat. No. 5,650,543 is incorporated herein by reference.

U.S. Pat. No. 6,313,182 issued to Lassila, et al. dated Nov. 6, 2001 entitled Acetylenic diol ethylene oxide/propylene oxide adducts and processes for their manufacture discloses water-based compositions, particularly coating, ink, fountain solution and agricultural compositions, manifesting reduced equilibrium and dynamic surface tension by the incorporation of a surface tension reducing amount of an acetylenic diol ethylene oxide/propylene oxide adduct. Also disclosed is a method for making random and block EO/PO adducts of acetylenic diols by reacting an acetylenic diol with EO and/or PO in the presence of a trialkylamine or Lewis acid. U.S. Pat. No. 6,313,182 is incorporated herein by reference as the preferred method of making the alkoxylated acetylenic materials of the present invention.

THE INVENTION

Objective of the Invention

It is the objective of the current invention to provide an acetylenic containing quaternary ammonium compound made by reaction epichlorohydrin with 2,4,7,9-tetramethyl-5-decyne-4,7-diol, followed by reaction with a tertiary amine.

It is also an object of the current invention to provide a process for conditioning hair, skin and textile fiber with the acetylenic quaternium ammonium compound of the present invention.

Other objectives will become clear as one reads the disclosure. All % shown herein are to be % by weight and all referenced patents are hereby incorporated herein by reference.

SUMMARY OF THE INVENTION

The present invention is directed to an acetylenic containing quaternary ammonium compounds (commonly called quats) made by reaction epichlorohydrin with 2,4,7,9-tetramethyl-5-decyne-4,7-diol, to produce an intermediate, followed by reacting the intermediate with tertiary amines to produce a quaternium ammonium compound (commonly called a quat).

The present invention is also directed to a process for conditioning hair, skin and textile fiber with the acetylenic ether amine of the present invention.

DETAILED DESCRIPTION OF THE INVENTION

The present invention is directed to an acetylenic quaternary ammonium compound conforming to the following structure:

$$(CH_3)_2-CH-CH_2-\underset{\underset{OR}{|}}{C(CH_3)}-C\equiv C-\underset{\underset{OR}{|}}{C(CH_3)}-CH_2-CH-(CH_3)_2$$

wherein:

$$R \text{ is } -(CH_2CH_2O)_m-(CH_2CH(CH_3)O)_n-CH_2CH(OH)CH_2-\underset{\underset{R^3}{|}}{\overset{\overset{R^1}{|}}{N^+}}-R^2\ Cl^-$$

wherein:

m and n are independently integers ranging from 0 to 20:

$R^1$ and $R^2$ are selected from the group consisting of $CH_3$ and $-(CH_2CH_2-O-)_x-(CH_2CH(CH_3)O)_yH$ $R^3$ is selected from the group consisting of $CH_3-(CH_2)_a$ and $CH_3-(CH_2)_b-C(O)-N(H)-(CH_2)_3-$ a is an integer ranging from 0 to 21;

b is an integer ranging from 9 to 21;

x and y are independently integers ranging from 1 to 20.

The present invention is also directed to a process for conditioning hair, skin and textile fibers which comprises contacting the hair, skin or textile fiber with an effective conditioning concentration of an acetylenic quaternary ammonium compound conforming to the following structure:

$$(CH_3)_2-CH-CH_2-\underset{\underset{OR}{|}}{C(CH_3)}-C\equiv C-\underset{\underset{OR}{|}}{C(CH_3)}-CH_2-CH-(CH_3)_2$$

wherein $$R \text{ is} -(CH_2CH_2O)_m-(CH_2CH(CH_3)O)_n-CH_2CH(OH)CH_2-\underset{\underset{R^3}{|}}{\overset{\overset{R^1}{|}}{N^+}}-R^2Cl^-$$

wherein:
m and n are independently integers ranging from 0 to 20;
$R^1$ and $R^2$ are selected from the group consisting of $CH_3$ and $-(CH_2CH_2-O-)_x-(CH_2CH(CH_3)O)_yH$
$R^3$ is selected from the group consisting of $CH_3-(CH_2)_a$ and
$CH_3-(CH_2)_b-C(O)-N(H)-(CH_2)_3-$
a is an integer ranging from 0 to 21;
b is an integer ranging from 9 to 21;
x and y are independently integers ranging from 1 to 20.

Said effective conditioning concentration ranges from 0.1 to 50% by weight.

Preferred Embodiments

In a preferred embodiment the process is directed to hair.
In a 'preferred embodiment the process is directed to skin.
In a preferred embodiment the process is directed to fiber.
In a preferred embodiment the effective conditioning concentration ranges from 1.0 to 10.0% by weight.
In a preferred embodiment the effective conditioning concentration ranges from 1.0 to 10.0% by weight.
In a preferred embodiment $R^1$ $R^2$ and $R^3$ are each $CH_3$.
In a preferred embodiment $R^1$ and $R^2$ are each $CH_3$ and $R^3$ is $CH_3-(CH_2)_a$.
In a preferred embodiment $R^1$ and $R^2$ are each $CH_3$ and $R^3$ is $CH_3-(CH_2)_b-C(O)-N(H)-(CH_2)_3-$
In a preferred embodiment $R^1$ and $R^2$ are each $-(CH_2CH_2-O-)_x-(CH_2CH(CH_3)O)_yH$ and $R^3$ is $CH_3-(CH_2)_a$.
In a preferred embodiment a is 0.
In a preferred embodiment a is an integer ranging from 11 to 21
In a preferred embodiment b is 11.

While not wanting to be bound by a specific theory for the enhanced performance of acetylenic quaternary ammonium compounds over traditional quats is that the performance is improved not only by the presence of the acetylenic moiety and the di-quaternary moiety, but more importantly by the location of these critical moieties in the molecule. Specifically the acetylenic group in the center and the Gemini quaternary groups in the terminal positions.

The structure of the compounds of the present invention have two critical required elements lacking in previous compounds. They are a terminal positively charged quaternium ammonium group and a central acetylenic group. This specific structure results in a very desirable conformation in aqueous solution. The molecule can be thought of as a horse shoe, in which the terminal ends have not only great water affinity, but also hair and skin affinity. In addition the critical acetylenic group, responsible for the lower surface tension is center of the horseshoe, maximizing the effect.

Traditional ether amines are quats contain a long fatty tail. This type of structure defats the skin and hair resulting in a hydrophobic greasy feeling. They totally lack the required acetylenic group that provides the lower surface tension. The very important effect the Gemini structure has on the orientation at the surface is the salient property of these molecules lacking in the compounds presently known.

The ethoxylates of 2,4,7,9-tetramethyl-5-decyne-4,7-diol, lack the critical positive quaternary group which is not only needed to maximize the effect upon surface tension but is critical to provide conditioning on hair, skin and fiber.

EXAMPLES

Example 1

2,4,7,9-tetramethyl-5-decyne-4,7-diol is an item of commerce conforming to the following structure:

$$(CH_3)_2-CH-CH_2-\underset{\underset{OH}{|}}{C(CH_3)}-C\equiv C-\underset{\underset{OH}{|}}{C(CH_3)}-CH_2-CH-(CH_3)_2$$

This material has a CAS number if 126-86-3. It is sold commercially as SURFYNOL® 104 SURFACTANT Example 2

Ethylene Oxide

Ethylene oxide is an item of commerce and has the CAS number 75-21-8.

Example 3

Propylene Oxide

Propylene oxide is an item of commerce and has the CAS number 75-56-9

Example 4

Epichlorohydrin

Epichlorohydrin is an item of commerce, and has a CAS number of 106-89-9.

Example 5

Dimethylethylamine

Dimethylethylamine is an item of commerce having the CAS Number: 598-56

Process 1 Alkoxylation of 2,4,7,9-tetramethyl-5-decyne-4,7-diol

U.S. Pat. No. 6,313,182 clearly teaches the conditions for alkoxylation of acetylenic diols. With respect to the processes for the preparation of acetylenic diol EO/PO adducts, the tertiary acetylenic diol starting materials can be prepared in various known manners such as those described in U.S. Pat. Nos. 2,250,445; 2,106,180 and 2,163,720, which are incorporated by reference. The acetylenic diol starting material may contain from 8 to 26 carbons. It is preferred that the acetylenic dial starting material contain 14 to 16 carbons, and it is most particularly preferred that it be 2,4,7,9-tetramethyl-5-decyne-4,7-diol.

Various basic catalysts can be used to promote the reaction between the alkylene oxide and the acetylenic tertiary glycols in which the hydroxyl groups are attached to a carbon atom in a position alpha to the acetylenic bonds according to this invention. Tertiary aliphatic amines, namely trialkylamines such as trimethylamine, triethylamine, tripropylamine, dimethylethylamine, diethylmethylamine and the like, are particularly advantageous catalysts for the reaction. Such tertiary aliphatic amines catalyze the addition reaction at a rapid rate at moderately low temperatures and pressures without inducing cleavage of the acetylenic glycol. Trimethylamine is preferred because of its high catalytic activity and longevity in the reaction.

As is known in the art, the use of strongly basic catalysts such as sodium hydroxide, especially at high temperatures of about 150.degree. C., induces cleavage of the acetylenic tertiary glycols and for this reason should be avoided, unless of course, sufficient ethylene oxide has been added to prevent substantial decomposition of tertiary acetylenic alcohol functionality. Once the tertiary hydroxyl groups of the acetylenic glycol have reacted with ethylene oxide, the resultant adduct exhibits the marked stability of an ether. So stable are the adducts that they can be heated with concentrated base such as sodium hydroxide at elevated temperatures, while comparable treatment of the initial acetylenic glycol is accompanied by extensive degradation. Consequently, strongly basic catalysts, such as the alkali metal hydroxides, can be used to increase the polyoxyalkylene chain length once the initial adducts have been formed and protected against decomposition. It is anticipated that alkali metal hydroxides could also be used to promote the addition of propylene oxide to initial EO or PO adducts with sufficiently low quantities of residual tertiary acetylenic alcohol functionality.

The trialkylamine-catalyzed addition reaction may be performed at either atmospheric (15 psig; 1 bar) or moderate to low super atmospheric pressures (30-300 psig; 2-20 bar). The use of moderate to low super atmospheric pressures is preferred since it obviates the necessity of recycling unreacted ethylene oxide and propylene oxide, and generally proceeds at faster rates than additions carried out at atmospheric pressures. The effect of pressure on rate is particularly important in the reaction with propylene oxide, and it is therefore preferred that reactions be performed at pressures in excess of 30 psig (2 bar). It is particularly preferred that the process be carried out at a pressure greater than 60 psig (4 bar). Another benefit of performing the reaction under pressure is that such reactions may be accomplished with ordinary efficient agitation, while reactions conducted at atmospheric pressure often work best when a dispersion type agitator is used. While the reaction can be carried out at lower pressure, reaction rates, and therefore reactor productivity, suffer. Performing the reaction at pressures much in excess of about 300 psig (20 bar) would likely have only marginal benefit, and would increase the cost of equipment required for manufacture. It is preferred to operate at 100 psig (6.7 bar).

The temperature at which the reaction is run for trialkylamine catalyzed reactions will depend upon the particular system and the catalyst concentration. Generally, at higher catalyst concentrations, the reactions can be run at lower temperatures and pressures. Reaction temperatures should be high enough to permit the reaction to proceed at a reasonable rate, but low enough to prevent decomposition of the reagents and products. Temperatures in the range of 40-150.degree. C. are suitable, 50-120.degree. C. preferred, and 70-90.degree. C. particularly preferred.

In the trialkylamine catalyzed process in which propylene oxide is added to an acetylenic diol EO adduct, the reaction stops at a PO end cap on each chain.

To prepare the EO/PO adducts of the invention, the acetylenic glycol is liquefied by melting and the catalyst is added with stirring. Ethylene oxide and/or propylene oxide are added as liquids with stirring and the reaction is concluded when the desired polyoxyalkylene chain length is reached as determined by gel permeation chromatography (GPC), high performance liquid chromatography (HPLC), nuclear magnetic resonance (NMR), cloud point (ASTM D2024-65) or water titration of an isopropyl alcohol solution. No solvents are necessary during the reaction, but inert solvents such as aromatic hydrocarbons (benzene and toluene) and ethers (ethyl ether) may be used to facilitate handling. In some instances it may be convenient to use a low mole ethoxylated acetylenic diol, since these products are liquids and are therefore easy to handle.

In reactions catalyzed by Lewis acids, the reaction conditions will be determined by the identity and concentration of the catalyst. Examples of Lewis acid catalysts include $BCl_3$, $AlCl_3$, $TiCl_4$, $BF_3$, $SnCl_4$, $ZnCl_2$ and the like. The preferred Lewis acid catalyst is $BF_3$. In $BF_3$ catalyzed reactions, temperature control during the initial stages of the reaction is critical, since too high a temperature will result in dehydration of the acetylenic diol. It is preferred that the temperature be maintained below 80 C., preferably below 60 C., and most preferably below 50 C. The reaction pressure can range from atmospheric to low to moderate super atmospheric pressure, i.e., from 15 to 300 psig (1 to 20 bar). Because of the high activity of $BF_3$, good results can be obtained at more moderate pressures of about 1 bar than for those reactions performed using trialkylamine catalysts.

In adding liquid alkylene oxide(s) to the acetylenic glycol and the catalyst, care should be taken to avoid the presence of an excess of alkylene oxide(s) in the reaction mixture since the reaction is very exothermic and could prove to be very hazardous. The danger of an uncontrollable reaction can be avoided by adding the alkylene oxide(s) in a manner and at a rate such that the alkylene oxide(s) are reacted essentially as rapidly as they are introduced into the reaction mixture. The formation of a flammable mixture in the headspace is best avoided by pressuring the reactor headspace to a sufficient pressure with an inert gas such as nitrogen such that the alkylene oxide(s) remains below its lower explosive limit (LEL).

Examples 6-16

A 1000 mL autoclave was charged the specified number of grams of 2,4,7,9teramethyl5decyene4,7diol (Example 1) and required number of grams of dimethylethylamine (Example 5) to equal 0.5% of the total weight of all reactants added. The reactor was sealed, purged free of air with three nitrogen pressure-vent cycles, then pressured to 100 psig (6.7 bar) with nitrogen and heated to 120.degree. C. Next add the specified number of grams of ethylene oxide or Propylene oxide over a period of 70 minutes by means of a syringe pump. At the completion of the addition, the reaction mixture was heated for an additional 12 hr at 120.degree. C. The reactor contents were cooled and discharged. The product was heated under vacuum to remove volatiles.

| Example | Diol Example 1 Grams | EO Example 2 grams | PO Example 3 grams | molesEO/molesPO |
|---|---|---|---|---|
| 6 | 335 | 44 | 59 | 1/1 |
| 7 | 335 | 220 | 59 | 5/10 |
| 8 | 335 | 440 | 295 | 10/5 |
| 9 | 335 | 660 | 59 | 15/1 |
| 10 | 335 | 880 | 1180 | 20/20 |
| 11 | 335 | 132 | 0 | 3/0 |
| 12 | 335 | 220 | 0 | 5/0 |

-continued

| Example | Diol Example 1 Grams | EO Example 2 grams | PO Example 3 grams | molesEO/ molesPO |
|---|---|---|---|---|
| 13 | 335 | 88 | 118 | 2/2/ |
| 14 | 335 | 0 | 236 | 0/4 |
| 15 | 335 | 0 | 0 | 0/0 |

The alkoxylates were filtered and used as raw materials for reaction with epichlorohydrin.

Process 2 Reaction of Alkoxylate with Epichlorohydrin

U.S. Pat. No. 5,098,979, incorporated herein by reference teaches the reaction of an alcohol with epichlorohydrin.

Place the indicated amount of the intermediate examples 6-16 in a suitable vessel. Add 0.5% by weight based upon the total weight of everything added during the reaction of $BF_3$ under good agitation and a nitrogen sparge. Next add 143.3 grams of epichlorohydrin (a molar excess of 0.5 of epichlorohydrin is added). The temperature is held between 100-115 degrees C. for two to six hours. The excess epichlorohydrin is stripped off under vacuum. Reaction progress is monitored by percent epoxide analysis and after stripping is very small.

| Example | Alkoxylate Example | Grams |
|---|---|---|
| 16 | 6 | 438 |
| 17 | 7 | 1145 |
| 18 | 8 | 1070 |
| 19 | 9 | 1054 |
| 20 | 10 | 2395 |
| 21 | 11 | 467 |
| 22 | 12 | 555 |
| 23 | 13 | 541 |
| 24 | 14 | 571 |
| 25 | 15 | 335 |

The halohydrin compound produced from this step conforms to the following structure and is converted to the quaternary compound in the next step:

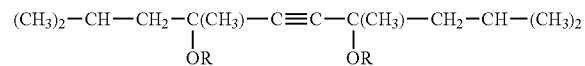

wherein
R is $-(CH_2CH_2O)_m-(CH_2CH(CH_3)O)_n-CH_2CH(OH)CH_2-Cl$
m and n are independently integers ranging from 0 to 20.

Preparation of Quaternium Compound
Tertiary Amine Raw Materials

One class of the tertiary amines used as a raw material in the preparation of the compounds of the present invention are alkyl dimethyl amine conforming to the following structure.

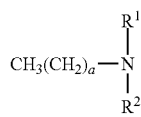

These materials are items of commerce available from a variety of sources including KAO, located in North Carolina, a is an integer ranging from 0 to 21.

| Example | a value |
|---|---|
| 26 | 0 |
| 27 | 11 |
| 28 | 13 |
| 29 | 17 |
| 30 | 21 |

A second class of the tertiary amines used as a raw material in the preparation of the compounds of the present invention are alkyl dimethyl amine conforming to the following structure.

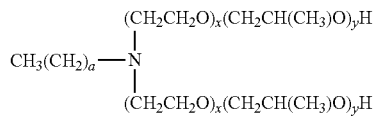

These materials are items of commerce available from a variety of sources.

x and y are integer ranging from 0 to 20 and a is an integer ranging from 0 to 21.

| Example | a value | x value | y value |
|---|---|---|---|
| 31 | 0 | 0 | 1 |
| 32 | 11 | 5 | 0 |
| 33 | 13 | 5 | 5 |
| 34 | 17 | 10 | 10 |
| 35 | 21 | 20 | 20 |

The third class of the tertiary amines used as a raw material in the preparation of the compounds of the present invention are alkyl dimethyl amine conforming to the following structure.

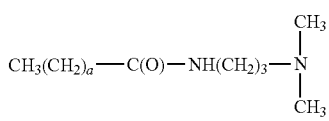

These materials are items of commerce available from a variety of sources including Colonial Chemical in South Pittsburg Tenn.

a is an integer ranging from 0 to 21.

| Example | a value |
|---|---|
| 36 | 10 |
| 37 | 12 |
| 38 | 16 |
| 39 | 20 |

Quaternary Compounds
General Procedure

A 1000 mL reaction vessel having heatain capabilities and a thermometer is charged the specified number of grams of the diol halohydrin intermediate (examples 16-25) and required number of grams of the required tertiary amine (Example 26-39) and the specified number of grams of water. The contents are heated to 80-90 C. for a 6-12 hr, until the chloride content approaches theoretical The reactor contents were cooled and discharged.

| | Diol Halohydrin | | Tertiary Amine | | Water |
|---|---|---|---|---|---|
| Example | Example | Grams | Example | Grams | Grams |
| 40 | 16 | 538 | 26 | 108 | 1292 |
| 41 | 17 | 1245 | 27 | 262 | 3014 |
| 42 | 18 | 1170 | 28 | 290 | 2920 |
| 43 | 19 | 1154 | 29 | 346 | 3000 |
| 44 | 20 | 2495 | 30 | 402 | 5794 |
| 45 | 21 | 567 | 31 | 226 | 1586 |
| 46 | 22 | 435 | 32 | 594 | 2058 |
| 47 | 23 | 541 | 33 | 121 | 1324 |
| 48 | 24 | 571 | 34 | 2298 | 5738 |
| 49 | 25 | 644 | 35 | 4477 | 10242 |
| 50 | 16 | 538 | 36 | 284 | 1644 |
| 51 | 17 | 1245 | 37 | 312 | 3114 |
| 52 | 18 | 1170 | 38 | 368 | 3076 |
| 53 | 19 | 1154 | 39 | 424 | 2792 |

Applications Examples

Depending upon the exact structure, the compounds of the present invention provide outstanding conditioning when applied to hair, Water soluble materials' can be applied in shampoo and body wash products, The dispersible products are applied in crème rinses.

The benefit is the low surface tension allows for easy spreadability and unique glide. The products also lower the surface tension provides outstanding wet comb.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. An acetylenic quaternary ammonium compound conforming to the following structure:

$$(CH_3)_2-CH-CH_2-\underset{\underset{OR}{|}}{C(CH_3)}-C\equiv C-\underset{\underset{OR}{|}}{C(CH_3)}-CH_2-CH-(CH_3)_2$$

wherein $$R \text{ is} -(CH_2CH_2O)_m-(CH_2CH(CH_3)O)_n-CH_2CH(OH)CH_2-\underset{\underset{R^3}{|}}{\overset{\overset{R^1}{|}}{N^+}}-R^2 \ Cl^-$$

wherein:
m and n are independently integers ranging from 0 to 20;
$R^1$ and $R^2$ are selected from the group consisting of $CH_3$ and $-(CH_2CH_2-O-)_x-(CH_2CH(CH_3)O)_yH$
$R^3$ is selected from the group consisting of $CH_3-(CH_2)_a$ and
$CH_3-(CH_2)_b-C(O)-N(H)-(CH_2)_3-$
a is an integer ranging from 0 to 21;
b is an integer ranging from 9 to 21;
x and y are independently integers ranging from 1 to 20.

2. An acetylenic quaternary ammonium compound of claim 1 wherein $R^1$ $R^2$ and $R^3$ are each $CH_3$.

3. An acetylenic quaternary ammonium compound of claim 1 wherein $R^1$ and $R^2$ are each $CH_3$ and $R^3$ is $CH_3-(CH_2)_a$.

4. An acetylenic quaternary ammonium compound of claim 1 wherein $R^1$ and $R^2$ are each $CH_3$ and $R^3$ is $CH_3-(CH_2)_b-C(O)-N(H)-(CH_2)_3-$.

5. An acetylenic quaternary ammonium compound of claim 1 wherein $R^1$ and $R^2$ are each $(CH_2CH_2-O-)_x-(CH_2CH(CH_3)O)_yH$ and $R^3$ is $CH_3-(CH_2)_a$.

6. An acetylenic quaternary ammonium compound of claim 1 wherein a is 0.

7. An acetylenic quaternary ammonium compound of claim 1 wherein a is an integer ranging from 11 to 21.

8. An acetylenic quaternary ammonium compound of claim 1 wherein b is 11.

* * * * *